US010302572B2

(12) United States Patent
Milesky et al.

(10) Patent No.: US 10,302,572 B2
(45) Date of Patent: May 28, 2019

(54) REAGENT CARD ALIGNMENT SYSTEM

(71) Applicant: Siemens Healthcare Diagnostics Inc., Tarrytown, NY (US)

(72) Inventors: Lawrence Milesky, Needham, MA (US); George N. Zantos, Medford, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 541 days.

(21) Appl. No.: 14/364,778

(22) PCT Filed: Dec. 14, 2012

(86) PCT No.: PCT/US2012/069621
§ 371 (c)(1),
(2) Date: Jun. 12, 2014

(87) PCT Pub. No.: WO2013/090655
PCT Pub. Date: Jun. 20, 2013

(65) Prior Publication Data
US 2014/0349409 A1  Nov. 27, 2014

Related U.S. Application Data

(60) Provisional application No. 61/576,503, filed on Dec. 16, 2011.

(51) Int. Cl.
*G01N 35/04* (2006.01)
*G01N 21/84* (2006.01)
(Continued)

(52) U.S. Cl.
CPC ......... *G01N 21/8483* (2013.01); *G01B 11/14* (2013.01); *G01N 21/253* (2013.01);
(Continued)

(58) Field of Classification Search
None
See application file for complete search history.

(56) References Cited

U.S. PATENT DOCUMENTS 3,918,910 A * 11/1975 Soya ................... G01N 21/8483
422/404
3,980,437 A 9/1976 Kishimoto et al.
(Continued)

FOREIGN PATENT DOCUMENTS

CN  201917571 U  8/2011
EP  0997715 A2  5/2000
(Continued)

OTHER PUBLICATIONS

Software translation of JP 2002-257837 (A) to Eiken Chemical, Sep. 11, 2002.*
(Continued)

Primary Examiner — Christopher Adam Hixson
Assistant Examiner — Michelle Adams
(74) Attorney, Agent, or Firm — Kyle D. Petaja

(57) ABSTRACT

A reagent card analyzer comprises an optical signal source configured to transmit an optical signal and an optical signal detector spaced a distance from the optical signal source to define an optical signal path into which the optical signal is transmitted, the optical signal detector configured to detect the optical signal and to output an electrical signal indicative of the optical signal. A reader is configured to read a reagent pad of a reagent card. A reagent card moving mechanism is configured to move the reagent card having the reagent pad including a leading and trailing end through the optical signal path. An optical detector interface is electrically coupled with the optical signal detector and configured to receive electrical signals and to output a pad detect signal (Continued)

indicative of at least one of the leading and the trailing end as the reagent card is moved through the optical signal path.

14 Claims, 10 Drawing Sheets

(51) Int. Cl.
*G01N 21/25* (2006.01)
*G01N 21/27* (2006.01)
*G01B 11/14* (2006.01)
*G01N 35/00* (2006.01)

(52) U.S. Cl.
CPC ....... *G01N 21/27* (2013.01); *G01N 35/00069* (2013.01); *G01N 35/04* (2013.01); *G01N 2035/00148* (2013.01); *G01N 2035/0491* (2013.01); *G01N 2035/0494* (2013.01); *G01N 2201/025* (2013.01); *G01N 2201/0438* (2013.01); *G01N 2201/06113* (2013.01)

(56) References Cited

U.S. PATENT DOCUMENTS

| | | | | |
|---|---|---|---|---|
| 4,345,193 | A * | 8/1982 | Barger | G01G 19/005 177/13 |
| 4,526,753 | A | 7/1985 | Boger et al. | |
| 5,114,350 | A | 5/1992 | Hewett | |
| 5,408,535 | A | 4/1995 | Howard, III et al. | |
| 6,736,553 | B1 * | 5/2004 | Stiehl | G02B 6/4246 385/89 |
| 6,750,962 | B2 | 6/2004 | Douglas et al. | |
| 2005/0237531 | A1 | 10/2005 | Roman | |
| 2007/0020143 | A1 * | 1/2007 | Seidenstricker | G01N 33/48764 422/400 |
| 2007/0183930 | A1 | 8/2007 | Roman | |
| 2011/0005932 | A1 | 1/2011 | Jovanovich et al. | |
| 2011/0223673 | A1 | 9/2011 | Profitt | |
| 2011/0243810 | A1 * | 10/2011 | Schosnig | G01N 33/48764 422/400 |

FOREIGN PATENT DOCUMENTS

| | | |
|---|---|---|
| GB | 1485506 A | 9/1977 |
| JP | S5132388 A | 3/1976 |
| JP | S5182685 A | 7/1976 |
| JP | S5430315 A | 3/1979 |
| JP | S55033544 A | 3/1980 |
| JP | S6375644 A | 4/1988 |
| JP | H01134262 A | 5/1989 |
| JP | H05302931 A | 11/1993 |
| JP | H0643996 A | 2/1994 |
| JP | H075110 A | 1/1995 |
| JP | H07190940 A | 7/1995 |
| JP | H09318544 A | 12/1997 |
| JP | 2000137028 A | 5/2000 |
| JP | 2000356597 A | 12/2000 |
| JP | 2002196009 A | 7/2002 |
| JP | 2002257837 A | 9/2002 |
| JP | 2005098937 A | 4/2005 |
| JP | 2007528491 A | 10/2007 |
| WO | 2011001201 A1 | 1/2011 |

OTHER PUBLICATIONS

European Search Report and Search Opinion of European Application No. EP 12857516 dated Nov. 6, 2015.

International Search Report and Written Opinion of International Application No. PCT/US2012/069621 dated Feb. 20, 2013.

European Examination Report of European Application No. 12857516.4 dated Apr. 4, 2018.

Japanese Office Action of Japanese Application No. 2018-025311 dated Dec. 4, 2018.

* cited by examiner

REAGENT CARD ALIGNMENT SYSTEM

INCORPORATION BY REFERENCE

The entirety of U.S. Provisional Application Ser. No. 61/576,503, filed on Dec. 16, 2011, is hereby expressly incorporated herein by reference.

BACKGROUND

1. Field of Inventive Concepts

The inventive concepts disclosed herein generally relate to non-contact position detection and more particularly, but not by way of limitation to optical position detection and analysis of reagent test pads for medical diagnostics via a reagent card alignment system.

2. Brief Description of Related Art

Reagent test strips are widely used in the fields of medicine and clinical chemistry. A test strip usually has one or more test areas, and each test area is capable of undergoing a color change in response to contact with a liquid specimen. The liquid specimen usually contains one or more constituents, substances, or properties of interest. The presence and concentrations of these constituents of interest in the specimen are determinable by an analysis of the color changes undergone by the test strip. Usually, this analysis involves a color comparison between the test area or test pad and a color standard or scale. In this way, reagent test strips assist physicians in diagnosing diseases and other health problems.

To satisfy the needs of the medical profession, as well as other expanding technologies, such as the brewing industry, chemical manufacturing, etc., a myriad of analytical procedures, compositions, and tools have been developed, including the so-called "dip-and-read" type reagent test devices. Regardless of whether dip-and-read test devices are used for the analysis of a biological fluid or tissue, or for the analysis of a commercial or industrial fluid or substance, the general procedure involves a test device coming in contact with the sample or specimen to be tested, and manually or instrumentally analyzing the test device.

Testing tools and methods have been sought in the art for economically and rapidly conducting multiple tests, especially via using automated processing. Automated analyzer systems have an advantage with respect to cost per test, test handling volumes, and/or speed of obtaining test results or other information over manual testing.

A recent development is the introduction of multiple-profile reagent cards and multiple-profile reagent card automated analyzers. Multiple-profile reagent cards are essentially card-shaped test devices which include a substrate and multiple reagent-impregnated pads (or matrices) positioned onto the substrate, for simultaneously or sequentially performing multiple analyses of analytes, such as the one described in U.S. Pat. No. 4,526,753, for example, the entire disclosure of which is hereby expressly incorporated herein by reference.

Multiple-profile reagent cards result in an efficient, economical, rapid, and convenient way of performing automated analyses. Automated analyzers configured to use multiple-profile reagent cards typically take a multiple-profile reagent card, such as from a storage drawer, or a cassette, and advance the multiple-profile reagent card through the analyzer over a travel surface via a card moving mechanism. The card moving mechanism may be a conveyor belt, a ratchet mechanism, a sliding ramp, or a card-gripping or pulling mechanism, for example. As the multiple-profile reagent card is moved or travels along the travel surface, one or more sample dispensers (e.g., manual or automatic pipette or pipette boom) may deposit or dispense one or more samples or reagents onto one or more of the reagent pads. Next, the multiple-profile reagent card may be analyzed (e.g., manually or automatically) to gauge the test result, such as via an optical imaging system, a microscope, or a spectrometer, for example. Finally, the used reagent card is removed from the analyzer, and is discarded or disposed of in an appropriate manner.

During the manufacturing of multiple-profile reagent cards, the reagent pads are generally attached in rows (e.g., to form one or more test strips) onto the substrate of the reagent card. However, typical manufacturing tolerances allow for a possible variance of about 2 mm of the positions of the rows of reagent pads relative to the substrate of the reagent card, with adjacent rows of reagent pads typically being separated by about 5 mm from one another.

Further, as reagent pads are generally rectangular in shape, it is optimal to deposit the sample substantially at the center of a reagent pad or at a central region of the reagent pad to help ensure thorough saturation of the reagent pad with sample, and to substantially prevent the sample from leaking out of the reagent pad and onto the substrate of the reagent card or into adjacent reagent pads.

Due to the need to precisely dispense the sample onto the reagent pad and the fact that reagent pad positions on the reagent card have relatively large manufacturing tolerances, it is important for automated analyzers to precisely locate the reagent pad on the multiple-profile reagent card prior to depositing the sample thereon.

Multiple prior art systems have attempted to resolve this problem without success. Several such systems are contact systems, which are complicated and inaccurate, and may cause misfeeding of reagent cards or damage to the reagent cards or reagent pads by contacting them.

To that end, a need exists in the prior art for a non-contact optical method and alignment system for precisely determining the positions of reagent cards and of one or more reagent pads on the reagent cards. It is to such optical card alignment systems and methods that the inventive concepts disclosed herein are directed.

SUMMARY

In one aspect the inventive concepts disclosed herein are directed to a reagent card analyzer comprising an optical signal source configured to transmit an optical signal having a strength and an optical signal detector spaced a distance from the optical signal source so that the optical signal source and the optical signal detector cooperate to define an optical signal path into which the optical signal source transmits the optical signal. The optical signal detector is configured to detect the optical signal and to output an electrical signal indicative of the strength of the optical signal. A reader is configured to read a reagent pad of a reagent card. A reagent card moving mechanism is configured to move one or more reagent card having the reagent pad including a leading end and a trailing end through the optical signal path and toward the reader. An optical detector interface is electrically coupled with the optical signal detector and is configured to receive electrical signals from the optical signal detector and to output a pad detect signal indicative of at least one of the leading end and the trailing end of the reagent pad as the reagent card is moved through the optical signal path.

The optical signal path may be at a first location, and a sample dispenser configured to dispense a volume of a sample may be positioned at a second location separated a known distance from the first location. The card moving mechanism may be configured to move the one or more reagent card so that the one or more reagent pad is positioned substantially at the second location based upon the pad detect signal. In some exemplary embodiments the one or more reagent pad may have a central region, and the sample dispenser may be configured to dispense a volume of a sample on the central region of the one or more reagent pad. The reader may include an imaging system configured to capture an image of the one or more reagent pad at a third location separated at a known distance from the first location. The card moving mechanism may be configured to move the one or more reagent card so that the one or more reagent pad is positioned substantially at the third location based upon the pad detect signal. The optical signal may have a wavelength of about 850 nanometers. The optical signal source may include a vertical cavity surface emitting laser. The vertical cavity surface emitting laser may be configured to transmit an optical signal including a beam having an angular spread of less than about 2°.

In another aspect, the inventive concepts disclosed herein are directed to a reagent card analyzer comprising an optical signal source attached to a support and configured to transmit an optical signal having a strength and an optical signal detector attached to the support and spaced at a distance from the optical signal source so that the optical signal source and the optical signal detector cooperate to define an optical signal path at a first location, the optical signal detector configured to detect the optical signal and to generate an electrical signal indicative of the optical signal. A reader is configured to read one or more reagent pad of a reagent card positioned at a second location a known distance from the first location. A sample dispenser is configured to dispense a volume of sample on the one or more reagent pad of the reagent card and is positioned at a third location. A card moving mechanism is configured to move the reagent card between the optical signal source and the optical signal detector so that the reagent card interferes with the optical signal, and to move the reagent card so as to position the one or more reagent pad substantially at the second and the third location. An optical detector interface is electrically coupled to the optical signal detector and is configured to receive electrical signals from the optical signal detector and to output a pad detect signal indicative of at least one of the leading end and the trailing end of the reagent pad as the reagent card is moved between the optical signal source and the optical signal detector. A controller is configured to control the reader, the sample dispenser, and the and moving mechanism, the controller electrically coupled with the optical detector interface, wherein the controller is configured to operate the card moving mechanism to move the one or more reagent card so that the one or more reagent pad is positioned substantially at the second location or substantially at the third location based upon the pad detect signal.

The one or more reagent pad may have a central region, and the sample dispenser may be configured to dispense a volume of a sample on the central region of the one or more reagent pad. The reader may include an imaging system configured to capture an image of the one or more reagent pad at the third location. The optical signal may have a wavelength of about 850 nanometers. The optical signal source may include a vertical cavity surface emitting laser. The vertical cavity surface emitting laser may be configured to transmit an optical signal including a beam having an angular spread of less than about 2°.

In yet another aspect, the inventive concepts disclosed herein are directed to a method comprising passing a reagent card having a sequence of reagent pads including leading and trailing ends through an optical signal path defined by an optical signal source and an optical signal detector spaced at a distance from one another. The method further comprises receiving an electrical signal from the optical signal detector by an optical detector interface electrically coupled to the optical signal detector and configured to receive electrical signals from the optical signal detector. The method also comprises outputting a sequence of pad detect signals indicative of at least one of the leading end and the trailing end of the sequence of reagent pads as the reagent card is moved through the optical signal path.

In yet another aspect, the inventive concepts disclosed herein are directed to a method comprising attaching an optical signal source and an optical signal detector to a support of an analyzer upstream of a sample dispenser to direct an optical signal across a predetermined card travel path within the analyzer, and coupling an optical detector interface to the optical signal detector and a controller of the analyzer, the optical detector interface configured to receive electrical signals from the optical signal detector and to output a pad detect signal indicative of at least one of a leading end and a trailing end of a reagent pad to the controller as a reagent card is moved between the optical signal source and the optical signal detector.

BRIEF DESCRIPTION OF THE DRAWINGS

Implementations of the inventive concepts disclosed herein may be better understood when consideration is given to the following detailed description thereof. Such description makes reference to the annexed pictorial illustrations, schematics, graphs, figures, or drawings. The drawings are not necessarily to scale, and certain features and certain views of the drawings may be shown exaggerated, to scale, or in schematic in the interest of clarity and conciseness. Like reference numerals in the figures may represent and refer to the same or similar element or function. In the drawings.

DETAILED DESCRIPTION

Figure 1:
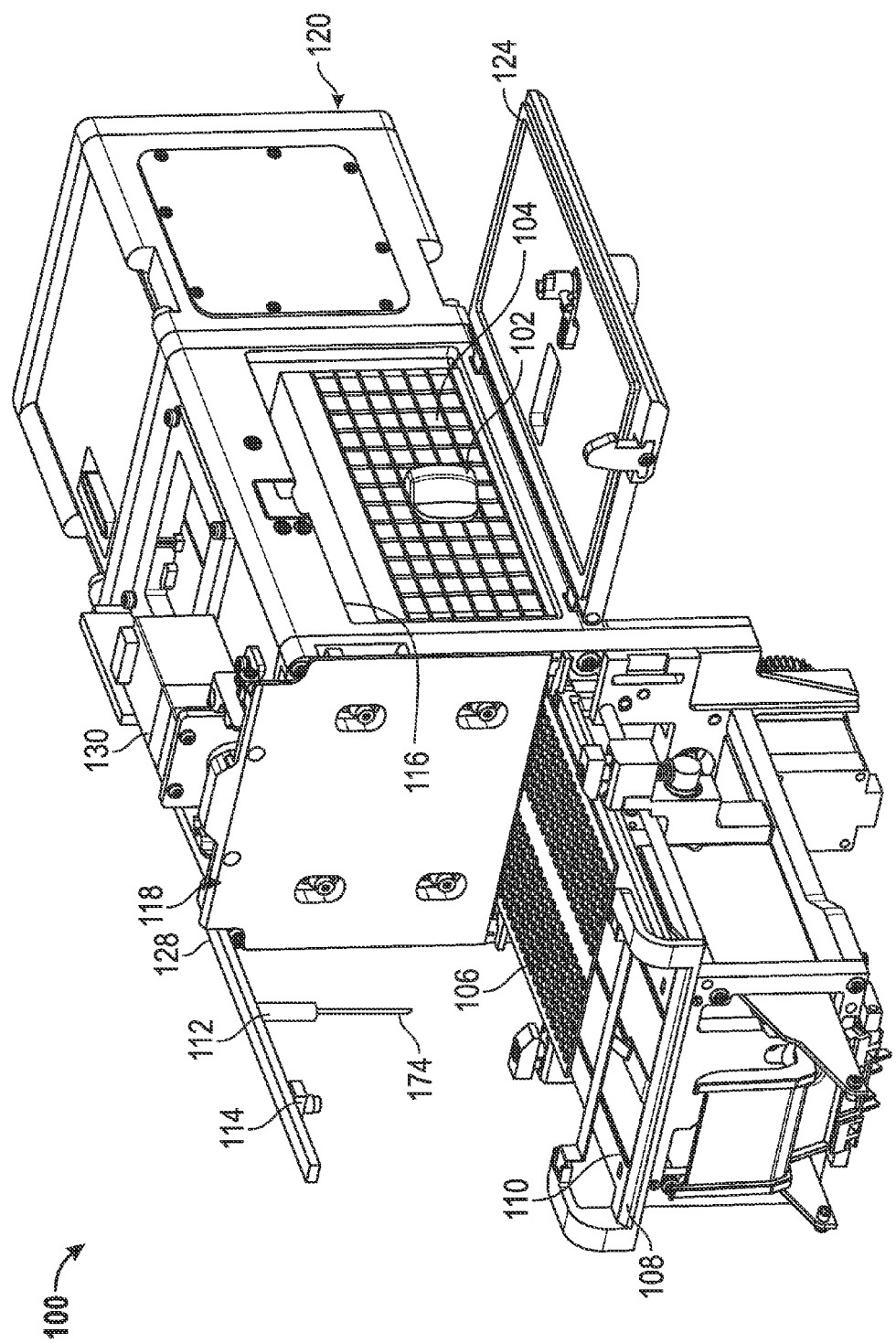
FIG. 1 is a perspective view of an exemplary embodiment of a card analyzer according to the inventive concepts disclosed herein with an external housing not shown for clarity.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Further, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Finally, as used herein qualifiers such as "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, and combinations thereof, for example.

The inventive concepts disclosed herein are generally directed to medical diagnostic systems, and more particularly, but not by way of limitation, to non-contact reagent card alignment systems and methods for making and using automated multiple-profile reagent card analyzers. In some exemplary embodiments of the inventive concepts disclosed herein, a non-contact method and system is disclosed to determine substantially exactly (within about less than 0.2 mm) the location of an edge of a substrate of a multiple-profile reagent card (hereinafter "reagent card," or "card") and the location of the ends of one or more reagent pads attached to the substrate of the reagent card.

The inventive concepts disclosed herein may employ an optical signal (e.g., a laser) based method to determine the positions of the edges of the substrate of the reagent cards and the ends of the reagent pads. For example, an optical signal source may be positioned above a surface on which a reagent card travels or is advanced, and an optical signal detector may be positioned below the surface of which the reagent card travels, such that the reagent card may be advanced along the surface and positioned between the optical signal source and the optical signal detector. The optical signal source may emit or transmit an optical signal which may be detected by the optical signal detector. When no reagent card is positioned between the optical signal source and the optical signal detector, the optical signal detected by the optical signal detector would be relatively strong, as there may only be air interfering with the optical signal as it travels between the optical signal source and the optical signal detector. The optical signal detector may detect the relatively strong optical signal and may generate a first electrical signal that is relatively strong and indicative of the relatively strong optical signal. The first electrical signal may be transmitted to an optical detector interface, as will be described below.

As a leading edge of a reagent card is advanced along the travel surface and is positioned at least partially between the optical signal source and the optical signal detector, the substrate of the reagent card begins interfering with the optical signal emitted by the optical signal source, causing a drop in the strength of the optical signal that reaches the optical signal detector. The substrate may be translucent plastic or other material that behaves as an optical diffuser, diffusing the optical signal between the optical signal source and the optical signal detector, for example. In response, the optical signal detector detects an optical signal which is relatively weaker compared to the relatively strong signal received when no card is present between the optical signal source and the optical signal detector. The optical signal detector may generate a second electrical signal that is relatively weaker and indicative of the relatively weaker optical signal. The optical signal detector may transmit the second electrical signal to an optical detector interface, for example.

As the reagent card is further advanced along the travel surface, a leading end of a reagent pad is positioned at least partially between the optical signal source and the optical signal detector and the reagent pad begins further interfering with the optical signal emitted by the optical signal source and causes a further drop in the strength of the optical signal that reaches the optical signal detector. The optical signal detector detects this relatively weaker optical signal and generates a third electrical signal indicative of the relatively weaker optical signal. The optical signal detector may transmit the third electrical signal to the optical detector interface, for example.

The difference between the second electrical signal and the third electrical signal may be very small, so the second electrical signal and the third electrical signal may be amplified, offset, or otherwise processed by the optical detector interface as will be described below, for example, to provide information indicative of which part of the reagent card, if any is positioned between the optical signal source and the optical signal detector.

The optical detector interface circuit may offset the incoming first, second, and third electrical signals by subtracting the range below the lowest measured signal from the received signal, and amplifying the resulting signal (e.g., about 2.5 times) to produce a processed signal indicative of the portion of a reagent card, if any, which is currently interfering with the optical signal, for example.

The substantially exact position of the leading edge of the substrate of the reagent card, and of the leading ends and trailing ends of the reagents pads may thus be detected and/or determined, and this information may be combined with the known location of a sample dispenser to operate the mechanism that advances the reagent card to substantially center the reagent pad under the sample dispenser by advancing the reagent card a certain distance over the travel surface, for example. A sample may be dispensed onto a central region of one or more reagent pad, for example. This information can also be combined with the known location of an imaging system, so that the reagent card may be advanced to any desired location or designated target area within a field of view of the imaging system, and one or more images of the reagent card and/or of the reagent pads may be captured by the imaging system, for example.

In one aspect, the inventive concepts disclosed herein, are directed to a card positioning system for an automated analyzer instrument that utilizes disposable multiple-profile reagent cards which have a substrate and a matrix of pads impregnated with various reagents positioned on a surface of the substrate. The reagent card and pads can be precisely aligned in order to dispense samples onto central regions of the pads for optimal sample distribution. In one example, the pads are bonded to the card with a possible variance of about 2 mm. An onboard optical system or other imaging system may then take digital pictures of the rows of pads, for example. The optical system may be configured as a medical diagnostic device that reads reagent cards, for example. The reagent cards may be stored in a stack or in a cassette in a reagent box, and may be incrementally advanced one reagent card at a time past a moisture protection gate. Once past the gate, bodily fluid samples such as urine may be deposited on each of the pads on the reagent card by a sample dispenser such as a pipette boom, for example. The analyzer may then advance the card to a target area to be imaged by the optical system.

In order for appropriate readings to be taken by the optical system, the device may determine and confirm the placement of the cards and the pads. In order to accomplish this, the device may be equipped with a card alignment system including an optical signal source such as a laser, and an optical signal detector that utilizes the differences in absorbance light levels between three different conditions of card movement. The detector may sense no card (zero absorbance), card edge or substrate (between about 99.90% and about 99.99% absorbance), and pad ends (an additional ≈30% on top of the 99.90% to 99.99% absorbance), for example. The optical properties of the card substrate may vary between a first lot of card substrate and a second lot of card substrate, and the card alignment system may be calibrated to each first card of a new lot or each new cassette as will be described below. The optical signal source may incorporate a special type of laser diode called a VCSEL which stands for Vertical Cavity Surface Emitting Laser, in some exemplary embodiments. This optical signal source may operate at an invisible wavelength of 850 nanometers and may possess a unique property of producing a narrow (e.g., less than about 2°) cylindrical beam which is very useful for making position measurements, for example. The optical signal source and optical signal detector may be placed above and below the reagent card travel surface to take appropriate readings in some exemplary embodiments.

Figure 2:
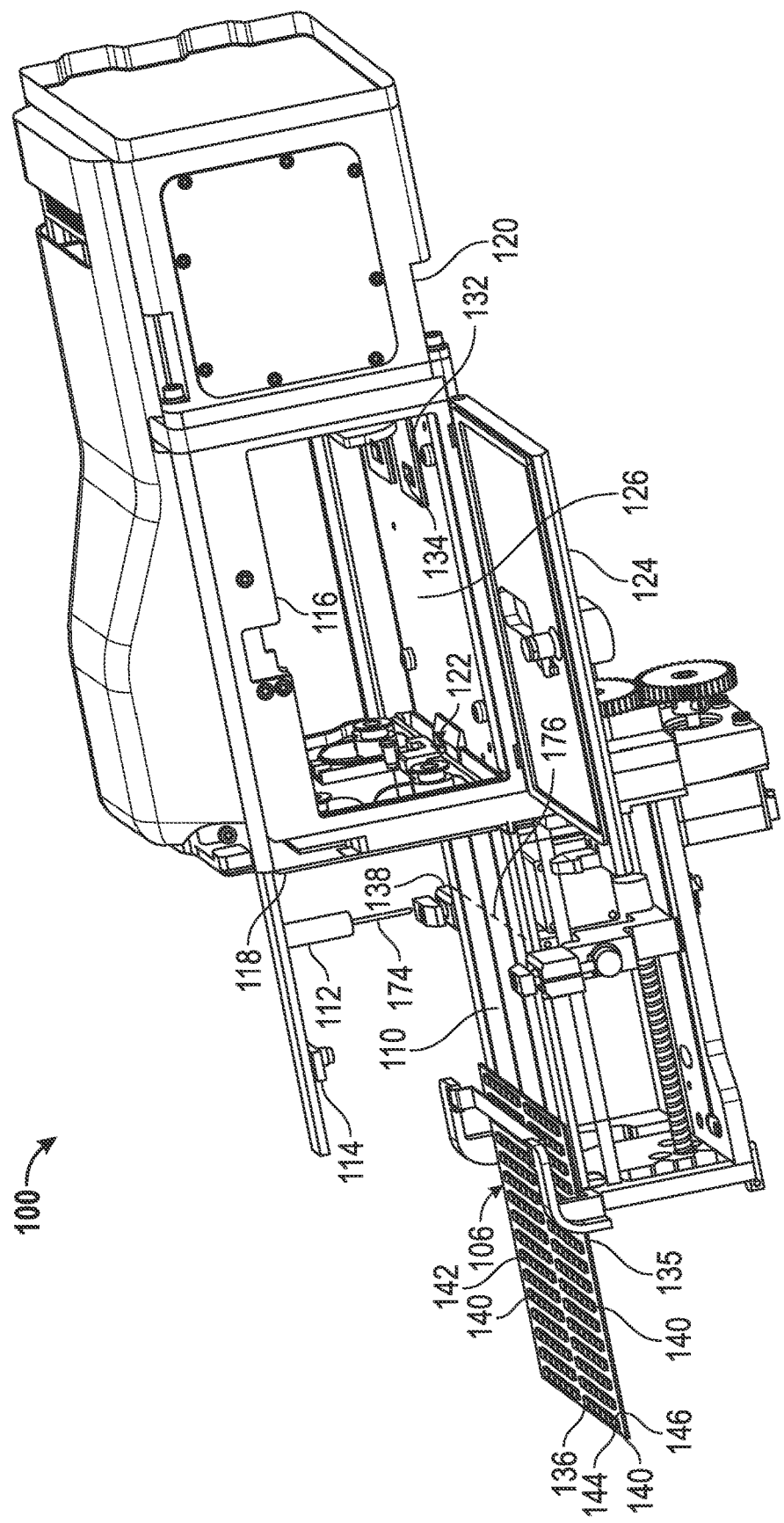
FIG. 2 is a perspective view of the card analyzer of FIG. 1, showing an exemplary embodiment of a card alignment system according to the inventive concepts disclosed herein.

Referring now to FIGS. 1-2, shown therein is a perspective view of an exemplary embodiment of an automatic analyzer 100 according to the inventive concepts disclosed herein. The analyzer 100 may include a storage compartment assembly 102 configured to accept a reagent card cassette 104 having one or more reagent cards 106 therein, a card travel assembly 108 configured to move a multiple-profile reagent card 106 along a travel surface 110 past a sample delivery assembly 112, and an imaging system 114, for example.

The storage compartment assembly 102 may include a storage compartment 116, a gate assembly 118, a card-stripping assembly 120, and a card alignment system 122, for example.

The storage compartment 116 may be implemented as any suitable housing configured to receive and store one or more reagent cards 106 therein, such that the one or more reagent cards 106 may be stripped or removed from the storage compartment 116 one at a time and may be advanced over the travel surface 110 as will be described below. The storage compartment 116 may be configured to receive and hold a stack of reagent cards 106 therein, or may be configured to receive a cartridge or a cassette 104 containing one or more reagent cards 106 therein, for example.

The storage compartment 116 may include a door 124 and a bottom 126. The door 124 may be implemented as any member that may be selectively opened and closed to allow access to the storage compartment 116 so that one or more reagent cards 106 or the cassette 104 may be introduced into or removed from the storage compartment 116. In some exemplary embodiments of the inventive concepts disclosed herein, the storage compartment 116 and the door 124 may be substantially vapor-tight, so as to protect any reagent cards 106 positioned inside the storage compartment 116 from vapors, moisture, or other contamination, as will be readily appreciated by a person of ordinary skill in the art having the benefit of the instant disclosure. Further, when the door 124 and a gate of the gate assembly 118 are substantially closed, the storage compartment 116 may be substantially opaque to light in the visible range, such that substantially no light in the visible range enter or exit the storage compartment 116, for example. Further, in some exemplary embodiments the storage compartment 116 may be substantially opaque to optical signals in the non-visible range, so that substantially no optical signals in the non-visible range may enter or exit the storage compartment 116.

The bottom 126 may be implemented as any suitable member, and may at least partially define the travel surface 110, as will be appreciated by persons of ordinary skill in the art having the benefit of the instant disclosure.

The gate assembly 118 may include a gate 128 operably coupled with a gate raising mechanism 130, for example. The gate 128 is shown as forming a part of the storage compartment 116, such that the gate 128 may be selectively opened and closed by the gate raising mechanism 130 to allow one or more reagent cards 106 to be advanced out of the storage compartment 116 and over the travel surface 110. In some exemplary embodiments, the gate 128 may also be configured as a vapor or moisture barrier, protecting the inside of the storage compartment 116 from moisture and contamination, for example. Further, the gate 128 may operate as a light barrier, such that substantially no light in the visible or optical signals in the non-visible range may enter or exit the storage compartment 116 when the gate 128 is substantially closed, for example.

The gate 128 may be operated by any suitable gate raising mechanism, such as the gate raising mechanism 130, which may be manual or automatic, and may include a gear mechanism, a servo, an electrical motor, an actuator, and combinations thereof, for example. In some exemplary embodiments a computer processor (not shown) executing processor executable code may operate the gate raising mechanism 130 to raise and lower the gate 128, and to operate the card-stripping assembly 120 to advance one or more reagent cards 106 partially or substantially completely past the gate 128 and onto the travel surface 110.

The card-stripping assembly 120 may extend at least partially into the storage compartment 116, and may be configured to strip, eject, advance, or otherwise remove a reagent card 106 from the storage compartment 116 (e.g., from a cassette 104 or from a stack of reagent cards 106), and advance such reagent card 106 at least partially past the gate 128, for example.

In some exemplary embodiments, the card-stripping assembly 120 may be configured to advance one or more reagent card 106 out of the storage compartment 116 and at least partially or substantially completely past the gate 128, when the gate 128 is partially or completely raised or open. In some exemplary embodiments, the gate 128 may be lowered onto the reagent card 106 as the reagent card 106 is partially advanced out of the storage compartment 116.

The card-stripping assembly 120 may include any suitable mechanism such as a conveyor belt, or a movable plate 132 having a card-stripping protrusion 134 formed therein, and combinations thereof, for example. The movable plate 132 may be moved along or adjacent to the bottom 126 of the storage compartment 116, such that the card-stripping protrusion 134 may engage with a trailing edge of a reagent card 106 and advance the reagent card 106 towards the gate 128 and at least partially past or beyond the gate 128 when the gate 128 is open or raised. As will be appreciated by persons of ordinary skill in the art, the movable plate 132 may be moved by any suitable moving mechanism, including a motor, a carriage, a servo, an actuator, or combinations thereof, for example. The moving mechanism may be configured to move the movable plate 132 along or adjacent to the bottom 126, for example.

It is to be understood that in some exemplary embodiments of the inventive concepts disclosed herein, the card-stripping assembly 120 may be omitted and one or more reagent card 106 may be advanced past the gate 128 in any desired manner, such as via gravity, conveyor belt, spring-loaded ejection mechanism, a ratchet mechanism, manually, and combinations thereof. Further, in some exemplary embodiments of the inventive concepts disclosed herein the storage compartment 116 may be omitted, and one or more reagent card 106 may be introduced onto the travel surface 110 in any suitable manner, including being manually inserted or fed into the analyzer 100, being provided in a roll, or combinations thereof.

The one or more reagent card 106 may include a substrate 135 with a leading edge 136, a trailing edge 138, and may have one or more reagent pads 140 positioned thereon, such that the one or more reagent pads 140 are aligned to define a test strip 142. As can be seen in FIG. 2, the reagent pads 140 may have a leading end 144 and a trailing end 146, and may be spaced apart a distance from one another.

Figure 3:
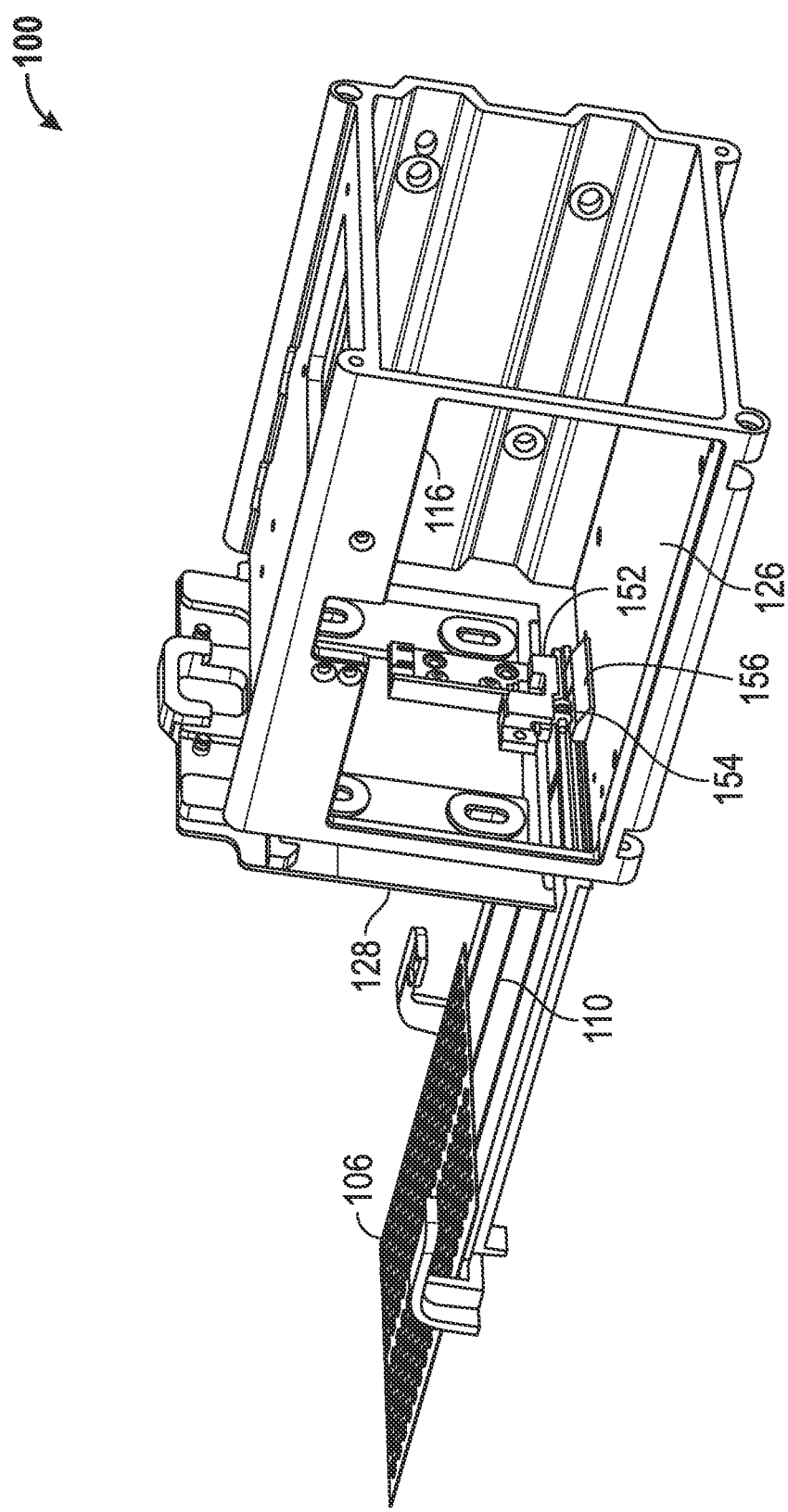
FIG. 3 is a partial perspective view of the card analyzer of FIG. 1, showing the card alignment system.
Figure 4:
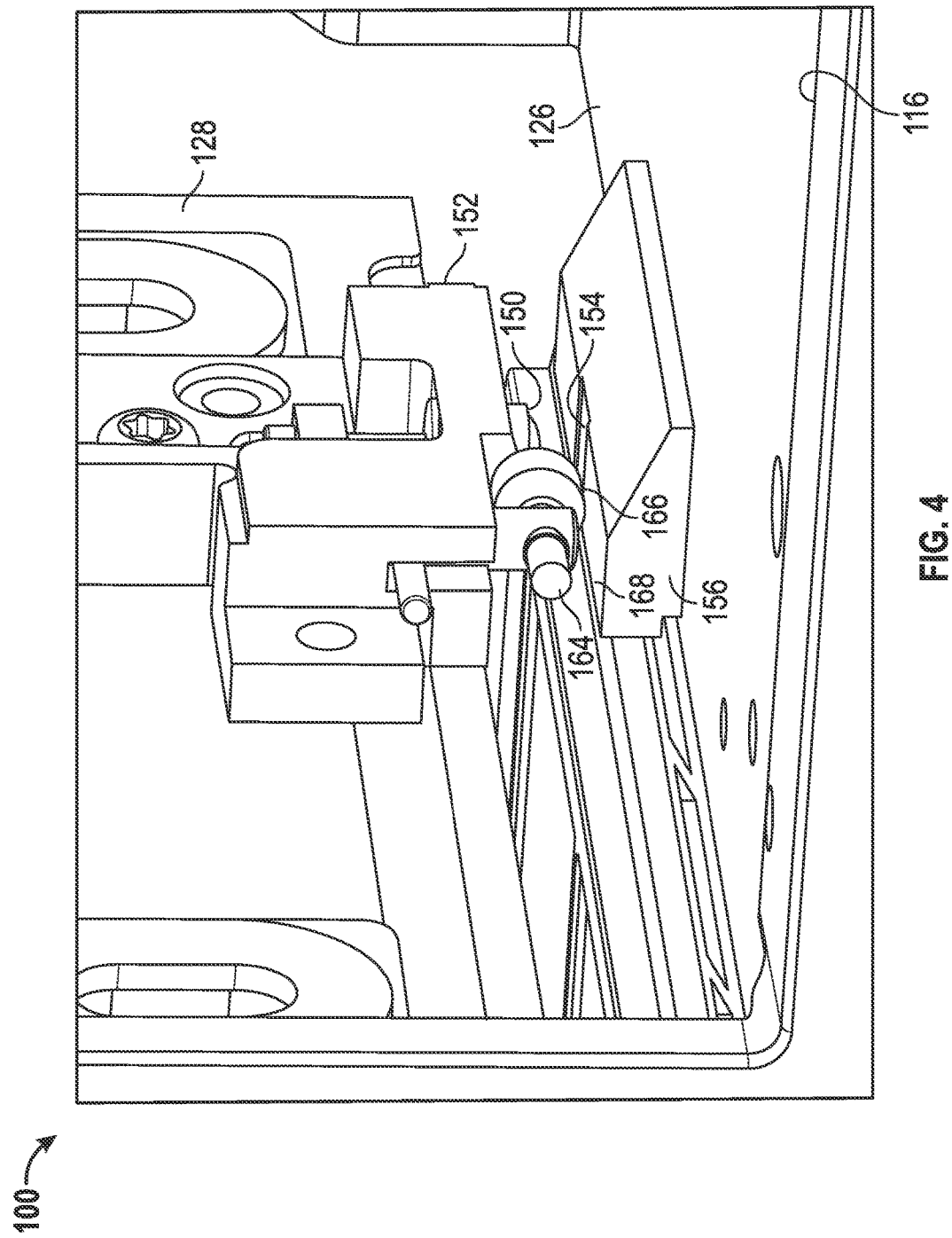
FIG. 4 is another partial perspective view of an exemplary embodiment of the card alignment system of FIG. 3.
Figure 5:
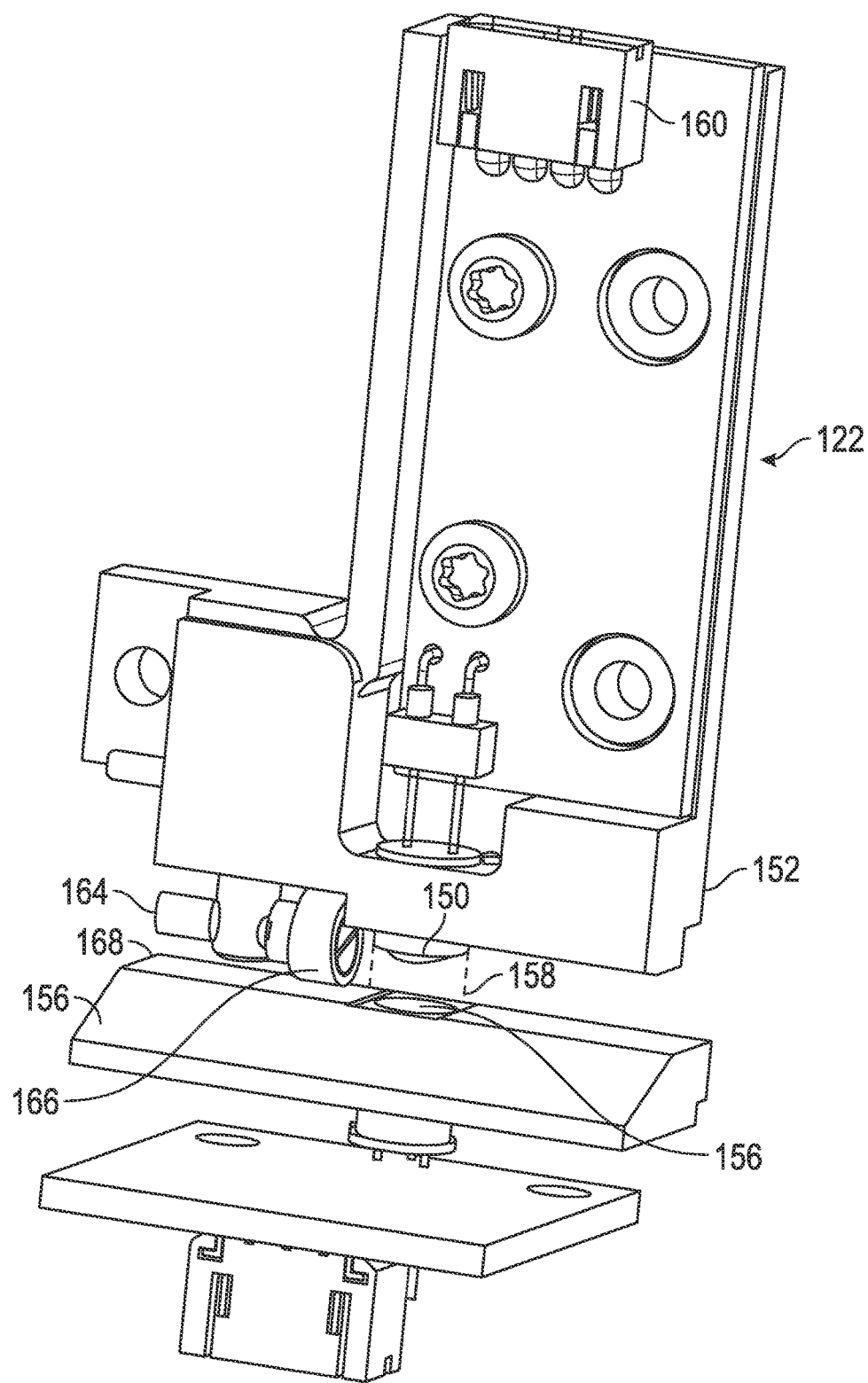
FIG. 5 is a perspective view of the card alignment system of FIG. 3.

Referring now to FIGS. 3-5, the card alignment system 122 may include an optical signal source 150 supported by a housing 152 which may be connected to the gate 128, and an optical signal detector 154 housed in a base 156 supported by the bottom 126 of the card storage compartment 116 so that the optical signal source 150 and the optical signal detector 154 are spaced a distance from one another, and so that the optical signal detector 154 is positioned at or below the travel surface 110, and the optical signal source 150 is positioned above the travel surface 110, or vice-versa, for example. The optical signal source 150 and the optical signal detector 154 may be aligned with one another so as to cooperate to define an optical signal path 158 (FIG. 5) therebetween, for example.

It is to be understood that in some exemplary embodiments of the inventive concepts disclosed herein, the optical signal source 150 may be supported by the bottom 126, and the optical signal detector 154 may be connected to the gate 128, as will be readily appreciated by a person of ordinary skill in the art. Further, it should be understood that in some exemplary embodiments, the optical signal source 150 and the optical signal detector 154 may be supported above and below the travel surface 110 to define the optical signal path 158 in any desired manner, such as by being connected to, or supported by any desired components or structure of the analyzer 100, provided that the reagent card 106 is at least partially positionable in the optical signal path 158 as the reagent card 106 is advanced towards the gate 128, past the gate 128, and/or along the travel surface 110, for example.

The optical signal source 150 may be implemented as any suitable device configured to emit or transmit an optical signal, such as a vertical cavity surface emitting laser, for example. The optical signal source 150 may be configured to emit an optical signal including a relatively narrow optical beam (e.g., having a relatively narrow angular spread of less than about 2°), and any desired wavelength such as a wavelength of about 850 nM, for example. In some exemplary embodiments of the inventive concepts disclosed herein, the optical signal source 150 may emit or transmit and optical signal having any desired wavelength, such as a wavelength varying between about 800 nM and about 900 nM, for example. It is to be understood that the optical signal source 150 may be implemented as any suitable device such as a light emitting diode, a laser, a quantum-well emitter, and may have any wavelength, including an adjustable wavelength and a substantially constant wavelength, and combinations thereof, for example. Further, the optical signal source 150 may emit any desired size optical beam, having an angular spread varying between about 0° to about 5°, or more, for example. As will be recognized by persons of ordinary skill in the art, the accuracy and precision of the card alignment system increases as the width and/or the angular spread of the optical beam emitted by the optical signal source 150 is reduced.

The optical signal source 150 may be attached to the housing 152 in any suitable manner, such as by adhesives, welds bolts, seams, joints, and combinations thereof, for example. In some exemplary embodiments, the optical signal source 150 and the housing 152 may be implemented as a unitary body, while in some exemplary embodiments the housing 152 may be omitted and the optical signal source 150 may be directly attached to the gate 128, or to any other desired component of the analyzer 100.

The housing 152 may likewise be attached to the gate 128 in any desired manner. An optional electrical connector 160 (FIG. 5) may be implemented as any desirable connector 160 and may be electrically coupled with the optical signal source 150 and with any suitable power source and/or control signal source (e.g., controller 162, FIG. 6) configured to power the optical signal source 150 and to control the strength of intensity of the optical signal emitted by the optical signal source 150, for example. As will be readily appreciated by a person of ordinary skill in the art having the benefit of the instant disclosure, it is desirable that the optical signal source 150 emits an optical signal having a relatively or substantially constant strength or intensity, although such strength or intensity may be adjustable to calibrate the card alignment system 122, for example. To that end, a controller 162 (FIG. 6) may be operably coupled with the optical signal source 150 and may be configured to ensure that the optical signal source 150 emits a substantially constant optical signal and/or to calibrate the optical signal source 150, for example, as will be described below.

As will be appreciated by persons of ordinary skill in the art having the benefit of the instant disclosure, the optical signal emitted by the optical signal source 150 may be processed, conditioned, filtered, diffused, polarized, or otherwise conditioned by one or more lenses (not shown), filters (not shown), collimators (not shown), diffusers (not shown), refractors (not shown), mirrors (not shown), prisms (not shown), and other devices, or combinations thereof, prior to being detected by the optical signal detector 154, for example.

Further, in some exemplary embodiments of the inventive concepts disclosed herein, the optical signal source 150 may be supported above the travel surface 110 in any desired manner, such as by being connected to the gate 128 in any desired manner (e.g., via joints, seams, bolts, brackets, fasteners, welds, or combinations thereof), or by the storage compartment 116, or by any other desired component of the analyzer 100, for example.

As will be appreciated by persons of ordinary skill in the art, in some exemplary embodiments of the inventive concepts disclosed herein, more than one optical signal source 150 may be implemented, such as two, or more than two optical signal sources 150.

An optional roller assembly 164 may be implemented with the housing 152 and may have a roller 166 configured to roll along the reagent card 106 as the regent card 106 is advanced through the optical signal path 158, so as to ensure that the substrate 135 of the reagent card 106 is maintained at a controlled distance from the optical signal source 150 and/or the optical signal detector 154 as the reagent card 106 travels into and through the optical signal path 158, for example. When no reagent card 106 is present between the optical signal source 150 and the optical signal detector 154, the optional roller assembly 164 may come into contact with the base 156 of the optical signal detector 154, for example. In some exemplary embodiments of the inventive concepts disclosed herein, the roller assembly 164 may be configured to operate as a switch, so that the optical signal source 150 is turned off when the roller assembly 164 is not in contact with the base 156 or with a reagent card 106, and so that the optical signal source 150 is turned on when the roller assembly 164 is in contact with the base 156 or with a reagent card 106, for example. The optional roller assembly 164 may be operably coupled with the controller 162 (FIG. 6), for example.

The optical signal detector 154 may be implemented as any device configured to detect optical signals and to convert optical signals into electrical signals, such as a silicon pin diode detector, charge-coupled device, or any other suitable device. The optical signal detector 154 is configured to detect an optical signal emitted by the optical signal source 150 and to generate an electrical signal indicative of the strength or intensity (or any other qualities, properties, or attributes) of the detected optical signal. For example, in some embodiments the optical signal detector 154 may generate electrical current which is proportional to the intensity or strength of the optical signal detected by the optical signal detector 154. Desirably, the optical signal detector 154 has a relatively narrow aperture, or detection area, such as an aperture or detection area of about 1 mm$^2$, for example, to improve a signal-to-noise ratio achieved by the optical signal detector 154. It is to be understood that other aperture sizes or detection areas may be used with the optical signal detector 154, varying from about 0 mm$^2$ to about 5 mm$^2$, or more, for example.

The optical signal detector 154 may be connected to the bottom 126, via the base 156, which may be implemented as a suitable support structure connected to the bottom 126 in any desired manner, such as via screws, adhesives, bolts, joints, seams, brackets, and combinations thereof, for example. The base 156 may have an upper surface 168 into which the optical signal detector 154 may be incorporated, for example. In some exemplary embodiments, the optical signal detector 154 may partially extend below or above the upper surface 168, as will be appreciated by persons of ordinary skill in the art. In some exemplary embodiments of the inventive concepts disclosed herein, the base 156 may be configured to allow one or more reagent cards 106 to slide over the base 156 as the reagent card 106 is advanced out of the storage compartment 116. Further, in some exemplary embodiments, the upper surface 168 of the base 156 may at least partially define the travel surface 110, or may be positioned substantially level with the travel surface 110 and adjacent thereto.

As will be appreciated by persons of ordinary skill in the art, in some exemplary embodiments, the base 156 may be omitted, or the base 156 and the bottom 126 may be formed as a unitary body. Further, in some exemplary embodiments of the inventive concepts disclosed herein, more than one optical signal detector 154 may be implemented, such as two, or more than two optical signal detectors 154.

The optical signal detector 154 may be operatively coupled with the controller 162 (FIG. 6), as will be described below.

Referring back to FIGS. 1-2, the card travel assembly 108 may be configured to move the reagent card 106 along the travel surface 110.

The card travel assembly 108 may include a movable card gripper 170 configured to move the reagent card 106 along the travel surface 110, such as by gripping the reagent card 106 and sliding, or otherwise advancing the reagent card 106 along the travel surface 110, for example. The card travel assembly 108 may move substantially longitudinally relative to the travel surface 110, such as via a movable carriage, for example. The card gripper 170 may be configured to grip, grasp, or otherwise engage a portion of the reagent card 106 as the reagent card 106 is advanced past the gate 128, for example.

The travel surface 110 may be supported by a base 172 and may be implemented as a substantially flat surface configured to allow the reagent card 106 to travel thereon, such as via sliding over the travel surface 110, for example. The travel surface 110 may extend substantially horizontally adjacent to the gate 128, such that a reagent card 106 advanced past the gate 128 may be advanced or otherwise travel over the travel surface 110. In some exemplary embodiments, the travel surface 110 may extend partially past the gate 128 and into the storage compartment 116, such that the gate 128 is lowered onto the travel surface 110, as will be appreciated by persons of ordinary skill in the art having the benefit of the instant disclosure.

The travel surface 110 may be constructed of any suitable material, such as plastics, metals, non-metals, thermoset materials, glass, resins, and combinations thereof, for example. The travel surface 110 may be constructed using any suitable technique such as injection molding, casting, machining, 3D printing, and combinations thereof, for example.

The sample delivery assembly 112 may be implemented as any desired system configured to deliver or dispense a volume of a sample onto a reagent pad 140 and/or a reagent card 106, and may include a sample dispenser 174 (e.g., an automated pipette boom, a manual pipette, a port, a syringe, a fluid pump, and combinations thereof). The sample dispenser 174 may be movably supported above the travel surface 110 and outside the storage compartment 116, so that the sample dispenser 174 may move laterally or transversely relative to the travel surface 110 along a line 176 for example. The sample dispenser 174 may deliver or dispense a volume of sample along the line 176 on the travel surface 110. The line 176 may be referred to as a sample delivery location or line, and a volume of a sample may be delivered or dispensed along any point along the line 176 by the sample dispenser 174 when a reagent card 106, reagent pad 140, or a test strip 142 is positioned thereon, for example.

The card alignment system 122 may function in combination with the card stripper assembly 120 to precisely position one or more reagent pads 140 or a test strip 142 on the line 176, so that a volume of sample may be deposited by the sample dispenser 174 onto the reagent pad 140 or test strip 142 substantially centered onto the line 176 and below the sample dispenser 174, as will be described in detail below. The sample may be deposited on a central region of the reagent pad 140, which central region may include a center of the reagent pad 140 and a region including or surrounding the center of the reagent pad 140 and extending around the center of the reagent pad 140 by between about 0 and about 50 percent of the width of the reagent pad 140 (e.g., the distance between the leading end 144 and the trailing end 146 of the reagent pad 140), for example. Depositing a volume of one or more samples substantially centered on the one or more reagent pads 140 may ensure that the deposited sample is substantially absorbed by the one or more reagent pad 140 and does not leak onto the substrate 135 of the reagent card 106, to avoid contaminating the reagent card 106 or adjacent reagent pads 140, as will be appreciated by a person of ordinary skill in the art having the benefit of the instant disclosure.

As will be appreciated by persons of ordinary skill in the art, in some exemplary embodiments of the inventive concepts disclosed herein, the sample dispenser 174 may be stationary, and/or two or more sample dispensers 174 may be positioned along the line 176 so that a volume of sample may be delivered by the two or more sample dispensers 174 to two or more reagent pads 140 positioned substantially centered on the line 176.

The imaging system 114 may be implemented and function as any desired reader, and may be supported at a location above the travel surface 110, so that an image of the reagent pads 140 may be captured by the imaging system 114, for example. The imaging system 114 may take an image of a reagent pad 140 at any desired target location or area along the travel surface 110, including the line 176, or any other desired location or area or multiple locations or areas, for example. As will be readily appreciated by a person of ordinary skill in the art, precisely positioning the reagent pad 140 on the line 176 would also allow the analyzer 100 to precisely position the reagent pads 140 of the reagent card 106 on any desired location along the travel surface 110, such that an image of any desired portion of the reagent card 106 or the reagent pads 140 may be taken by the imaging system 114. In some exemplary embodiments, the imaging system 114 may take an image of the reagent pads 140 as the reagent pads 140 are positioned onto the line 176, while in some exemplary embodiments the imaging system 114 may take an image of the reagent pads 140 as they are advanced past the line 176, and combinations thereof. Further, the imaging system 114 may take an image of the reagent pads 140 as the reagent pads 140 are positioned on a designated target location or area (not referenced) on the travel surface 110, which designated target location or area may be any location or area of the travel surface 110, including the line 176, for example.

The imaging system 114 may include any desired digital or analog imager, such as a digital camera, an analog camera, a CMOS imager, a diode, and combinations thereof. The imaging system 114 may also include any desired illumination source and/or lens system, for example. Further, the imaging system 114 is not limited to an optical imaging system in the visible spectrum, and may include a microwave imaging system, an X-ray imaging system, and other desired imaging systems, for example.

Figure 6:
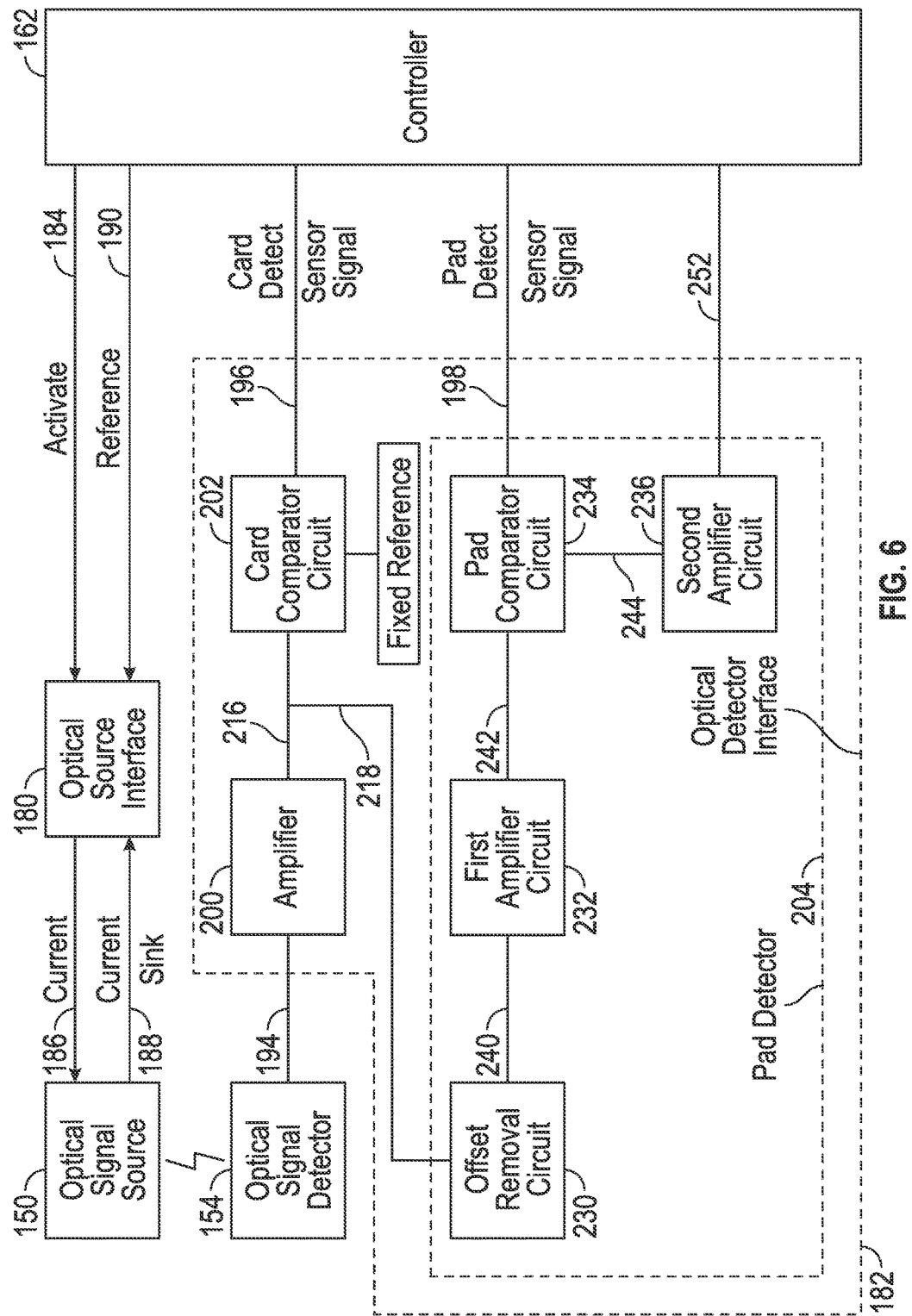
FIG. 6 is a diagram of an exemplary embodiment of a controller for the card alignment system according to the inventive concepts disclosed herein.
Figure 7:
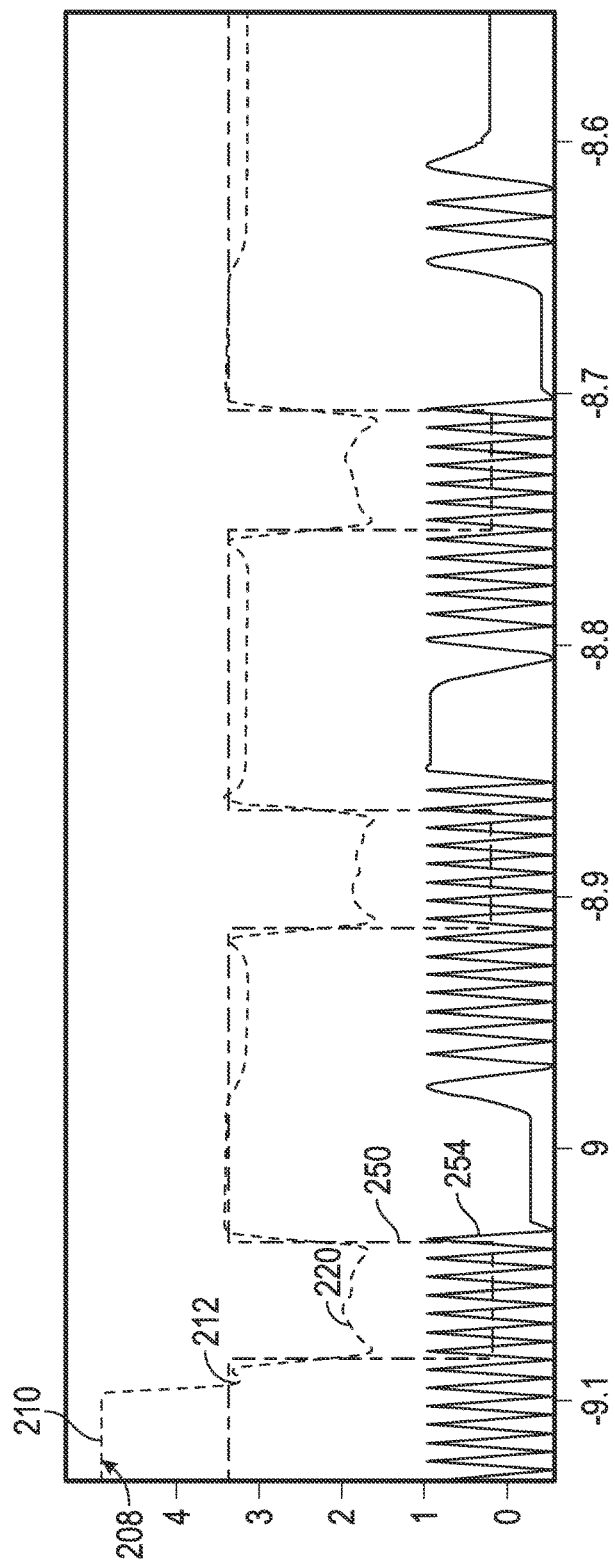
FIG. 7 is a graph showing an electrical sign processed by a signal comparator circuit according to the inventive concepts disclosed herein.
Figure 8:
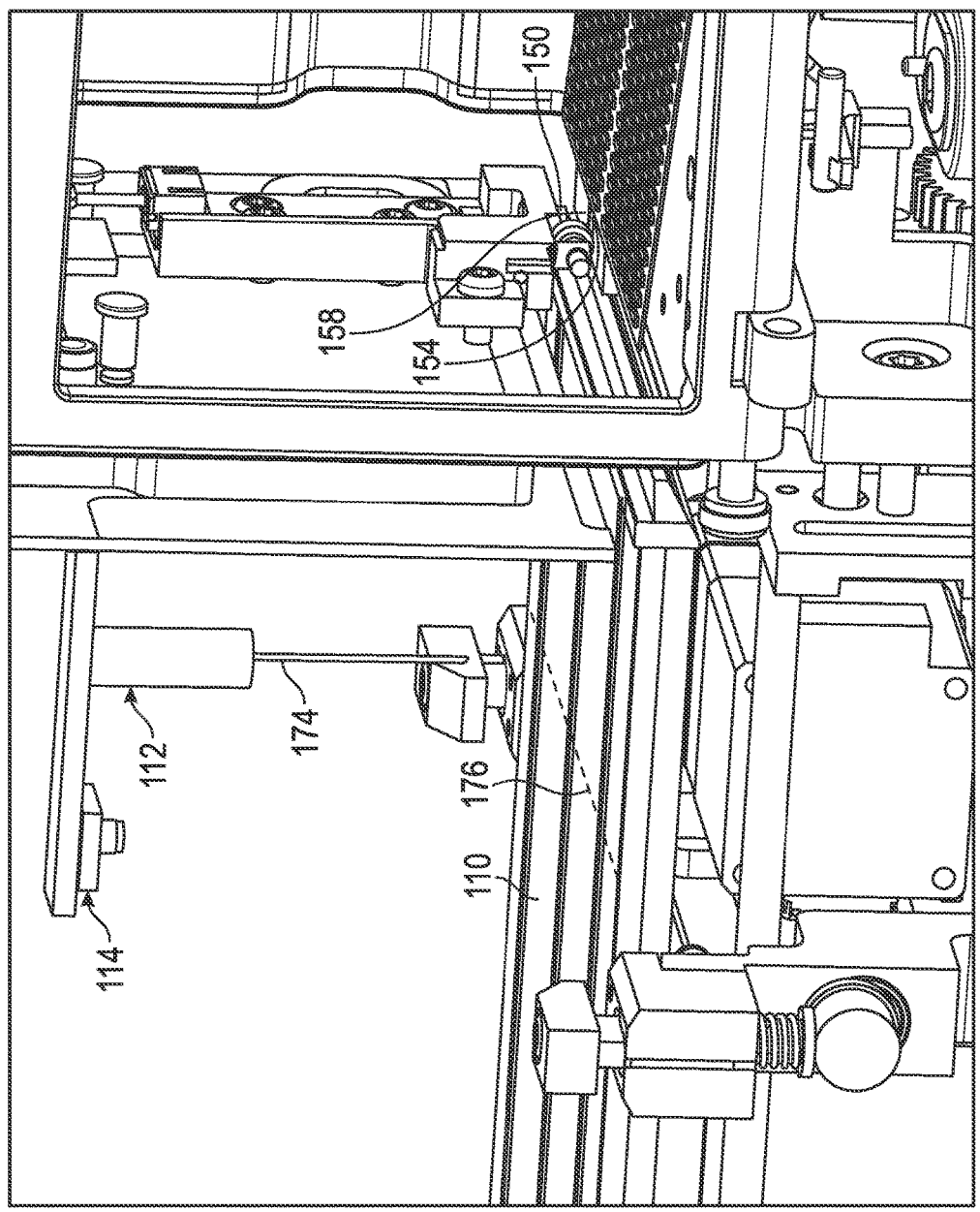
FIG. 8 is a partial perspective view of an analyzer according to the inventive concepts disclosed herein, with an edge of the card positioned between an optical signal source and an optical signal detector of a card alignment system thereof.
Figure 9:
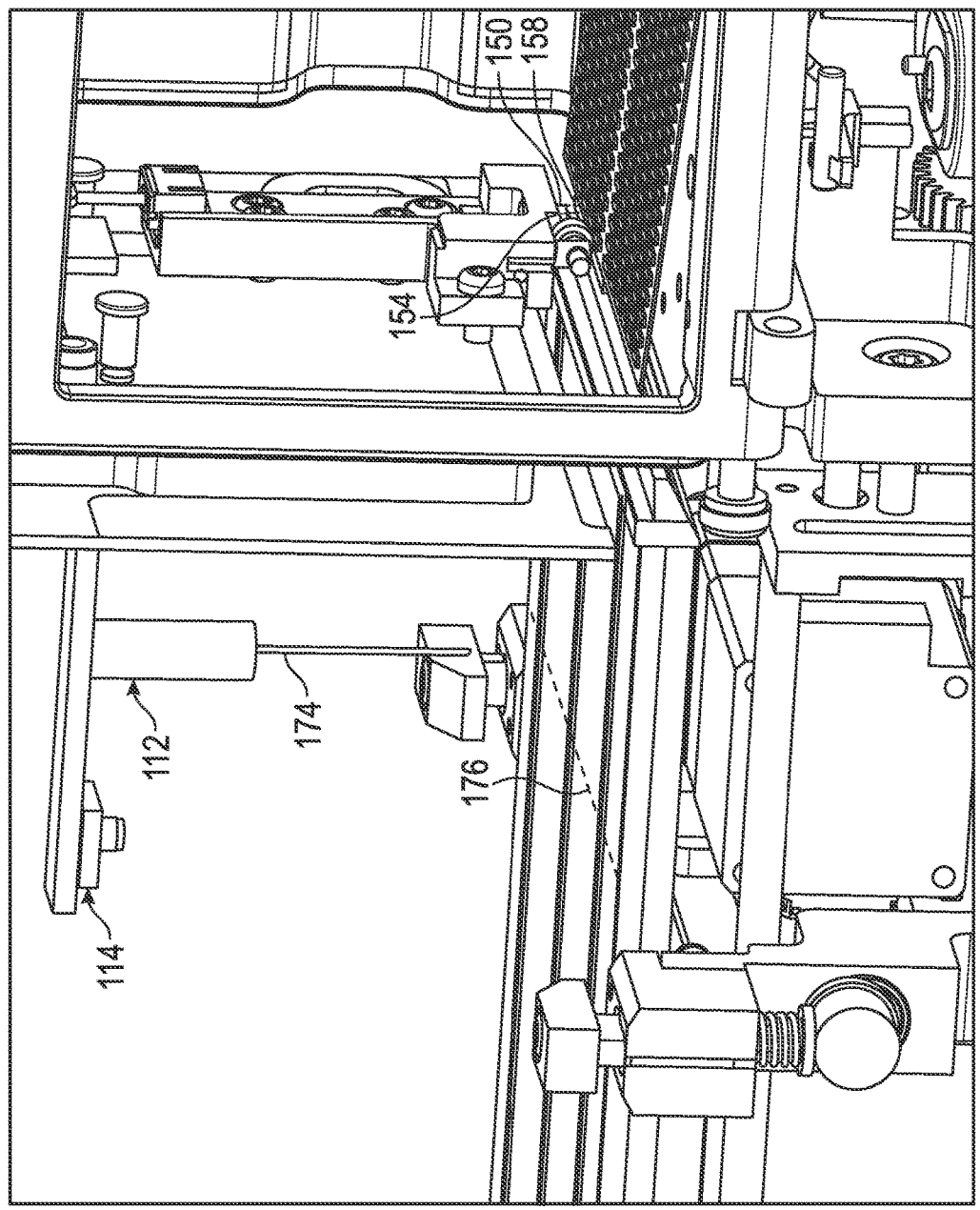
FIG. 9 is a partial perspective view of the analyzer of FIG. 8 with a leading end of a pad shown positioned between the optical signal source and the optical signal detector of a card alignment system thereof.

Referring now to FIGS. 6-7, the analyzer 100 may be provided with an optical source interface 180, and an optical detector interface 182. In general, the optical source interface 180 includes analog and/or digital circuitry that receives an activation signal from the controller 162 via a control line 184. Upon receipt of the activation signal from the controller 162, the optical source interface 180 generates a control signal and supplies the control signal to the optical signal source 150 via control lines 186 and 188. In particular, the control signal can be either a predetermined current signal, or a predetermined voltage signal depending upon the construction of the optical signal source 150, for example. In either case, the control signal may be controlled to provide a constant magnitude or strength such that the optical signal generated and emitted by the optical signal source 150 includes a substantially fixed and predetermined magnitude or strength, for example. In one embodiment, the control line 186 provides a predetermined amount of current to the optical signal source 150 while the control line 188 serves as a current sink for the optical signal source 150, for example. Optionally, the controller 162 may be electrically coupled to the optical source interface 180 via a control line 190 such that the controller 162 may supply a reference signal to the optical source interface 180. The reference signal can be used by the optical source interface 180 to set a magnitude of the control signal supplied to the optical signal source 150.

In general, the optical detector interface 182 may include analog and/or digital circuitry that receives a signal from the optical signal detector 154 via a line 194 and interprets the signal to provide a card detect sensor signal to the controller 162 via a control line 196, and a pad detect sensor signal to the controller 162 via a control line 198. The signal received from the optical signal detector 154 is desirably an electrical signal that has linear properties relative to a magnitude or strength of the optical signal provided by the optical signal source 150. In one embodiment, the optical signal detector 154 is a photodiode. In any event, the signal received from the optical signal detector 154 may be an electrical signal whose magnitude is indicative of an intensity or strength of the optical signal received by the optical signal detector 154.

In one embodiment, the optical detector interface 182 is provided with an amplifier 200, a card comparator circuit 202, and a pad detector circuit 204. The electrical signal generated by the optical signal detector 154 is fed to the amplifier 200 by the line 194. The amplifier 200 receives the electrical signal and amplifies the electrical signal such that changes in the electrical signal can be interpreted by the card comparator circuit 202 to detect the leading and trailing edges 136 and 138 of the substrate 135, and interpreted by the pad detector circuit 204 to detect the leading and trailing ends 144 and 146 of the reagent pads 140. The amplifier 200 may include an operational amplifier that is configured to be an inverting current to voltage amplifier.

Shown in FIG. 7 is a waveform 208 indicative of an exemplary output of the amplifier 200. As discussed above, the leading edge 136 of the substrate 135 is advanced along the travel surface 110 and is positioned at least partially between the optical signal source 150 and the optical signal detector 154 (e.g., in the optical signal path 158), the substrate 135 of the reagent card 106 begins interfering with the optical signal, causing a drop in the strength of the optical signal that reaches the optical signal detector 154. The amplifier 200 may be designed such that a first electrical signal 210 generated by the amplifier 200 is saturated in the absence of the reagent card 106 positioned between the optical signal source 150 and the optical signal generator 154. In the example shown, the voltage of the first electrical signal 210 is approximately 5 V.

The substrate 135 may be translucent plastic that behaves as an optical diffuser, diffusing the optical signal between the optical signal source 150 and the optical signal detector 154, for example. In response, the optical signal detector 154 receives an optical signal which is relatively weaker compared to the relatively strong signal received when no reagent card 106 is present between the optical signal source 150 and the optical signal detector 154. The optical signal detector 154 may generate a signal that is relatively weaker and indicative of the relatively weaker optical signal. The optical signal detector 154 may transmit the signal to the amplifier 200 via the line 194. In response thereto, the amplifier 200 generates a second electrical signal 212, which in the example shown in FIG. 7 has a voltage level between about 3 and about 3.5 V.

Electrical signals generated by the amplifier 200, including the first and second electrical signals 210 and 212 are provided to the card comparator circuit 202 via a line 216, and to the pad detector circuit 204 via line 218. In general, the card comparator circuit 202 may include analog and/or digital circuitry to form a comparator to compare the magnitude of the electrical signals generated by the amplifier 200 and a fixed or programmable reference voltage. In the example depicted in FIG. 6, a fixed reference voltage is provided to the card comparator circuit 202. The fixed reference voltage is selected to have a magnitude between the first electrical signal 210 and the second electrical signal 212, e.g., between about 5 V and about 3.5 V. In this example, the fixed reference voltage is selected to be about 4.5 V such that the card comparator circuit 202 will detect the leading edge 136 of the substrate 135. The output of the card comparator circuit 202 is provided to the controller 162 via the control line 196 and the controller 162 monitors the control line 196 to determine when the leading edge 136 of the substrate 135 enters the optical signal path 158.

As the reagent card 106 is further advanced along the travel surface 110, a leading end 144 of a reagent pad 140 is positioned at least partially between the optical signal source 150 and the optical signal detector 154 (e.g., in the optical signal path 158) and the reagent pad 140 begins further interfering with the optical signal and causes a further drop in the strength of the optical signal that reaches the optical signal detector 154. The optical signal detector 154 detects this relatively weaker optical signal and generates an electrical signal indicative of the relatively weaker optical signal. The optical signal detector 154 may transmit the electrical signal to the amplifier 200 of the optical detector interface 182. In response thereto, the amplifier 200 generates a third electrical signal 220 as shown in FIG. 7.

The difference between the second electrical signal 212 and the third electrical signal 220 may be very small, so the second electrical signal 212 and the third electrical signal 220 may have an electrical offset removed, followed by amplification to amplify the difference between the second electrical signal 212 and the third electrical signal 220 in order to aid the detection of the leading end 144 and the trailing end 146 of the reagent pad 140 by the pad detector circuit 204.

In the embodiment depicted in FIG. 6, the pad detector circuit 204 is provided with an offset removal circuit 230, a first amplifier circuit 232, a pad comparator circuit 234, and a second amplifier circuit 236. The offset removal circuit 230 may be electrically coupled to the first amplifier circuit 232 via a line 240. The first amplifier circuit 232 may be electrically coupled to the pad comparator circuit 234 via a line 242. The second amplifier circuit 236 may be electrically coupled to the pad comparator circuit 234 via a line 244.

In general, the offset removal circuit 230 is configured to remove a fixed or programmable amount of voltage from the electrical signals output by the amplifier 200 in order to increase the sensitivity of the pad detector circuit 204 as discussed above. The output of the offset removal circuit 230 is fed to the first amplifier circuit 232 via the line 240. The first amplifier circuit 232 receives the output of the offset removal circuit 230 and serves to amplify the output of the offset removal circuit 230. The amplified signal from the first amplifier circuit 232 is provided to the pad comparator circuit 234 via the line 242. And, a reference voltage generated by the second amplifier circuit 236 is provided to the pad comparator circuit 234 via the line 244.

The pad comparator circuit 234 receives the electrical signals via the lines 242 and 244 and compares the magnitudes of such signals in order to generate a pad detect sensor signal 250 that is shown by way of example in FIG. 7. The pad detect sensor signal is provided to the controller 162 via the control line 198. The level of the reference signal provided to the pad comparator circuit 234 from the second amplifier circuit 236 may be controlled by the controller 162 using a control line 252.

In one embodiment, the offset removal circuit 230 is configured to remove 1.235 V from the electrical signals supplied by the amplifier 200; the first amplifier circuit 232 is configured to amplify the electrical signal from the offset removal circuit 230 by a factor of 3.57; and the second amplifier circuit 236 is configured to amplify an electrical signal from the controller 162 by a factor of 2.0, for example. As will be understood by one skilled in the art, the parameters including the amount of offset, and the amplification factors used by the first amplifier circuit 232 and the second amplifier circuit 236 can be varied and/or calibrated based upon particular types of reagent cards 106 to be processed by the analyzer 100. For example, the offset removal circuit 230 may offset the incoming signals by subtracting the range below the lowest measured signal from the received signal, and amplifying the resulting signal (e.g., about 2.5 times) to produce a processed signal indicative of the portion of a reagent card, if any, which is currently interfering with the optical signal or is positioned in the optical signal path 158.

The substantially exact position of the leading edge 136 of the substrate 135 of the reagent card 106, and of the leading ends 144 and the trailing ends 146 of the reagents pads 140 may thus be detected, and this information may be combined with the known location of the sample dispenser 174 to operate the card travel assembly 108 and/or the card stripping assembly 120 to advance the reagent card 106 to substantially center the reagent pad 140 under the sample dispenser 174 (e.g., on the line 176) by advancing the reagent card 106 a certain distance over the travel surface 110, for example. Substantially centered should be understood to include the reagent pad 140 being centered over the line 176, and to also include the reagent pad 140 being centered over the line 176 with a variance of between about 0 and about 30 percent of the width of the reagent pad 140, for example. Further, this information may be combined with the known location of the imaging system 114 to position one or more reagent pad 140 at a designated target location or area along the travel surface 110 so that the imaging system 114 may take one or more images or videos of one or more reagents pads 140, for example.

Thus, the controller 162 receives a card detect sensor signal indicative of an exact position of the leading edge 136 and the trailing edge 138 of the substrate 135; as well as a pad detect sensor signal indicative of the exact position of the leading end 144 and the trailing end 146 of the reagent pads 140 supported by the substrate 135. The controller 162 may also correlate the information received from the card detect sensor signal and the pad detect sensor signal with information from the card travel assembly 108. For example, when the card travel assembly 108 includes a threaded mechanism for moving the reagent card 106, the controller 162 may count rotations of the threaded mechanism to determine a number of turns of the threaded mechanism used for advancing the reagent card 106 from the leading end 144 to the trailing end 146 of the reagent pads 140. For example, a waveform showing a signal 254 used to monitor rotation of the threaded mechanism is shown in FIG. 7. In the example shown, seven rotations of the threaded mechanism is used to move the reagent card 106 from a first position where the leading end 144 is within the optical signal path 158 to a second position where the trailing end 146 is within the optical signal path 158. This information allows the controller 162 and the analyzer 100 to calculate and determine the width of a reagent pad 144 by measuring the distance between the leading end 144 and the trailing end 146 of the reagent pad 140, for example.

The number of rotations for moving the reagent card 106 from the leading end 144 to the trailing end 146 of the pad 140 can be used by the controller 162 to operate the mechanism of the card travel assembly 108 that advances the reagent card 106 to substantially center the reagent pad 140 under the sample dispenser 174, or to move the reagent pad to a designated location for the imaging system 114 to take an image of the reagent pad 140, for example.

As will be appreciated by persons of ordinary skill in the art, the stock from which the substrate 135 of a reagent card 106 is made may vary its absorbance between about 99.90% and about 99.99%. Accordingly, a calibration of the strength or magnitude of the optical signal emitted by the optical signal source 150 may be performed by the optical source interface 180 and/or the controller 162 with each new cassette 104 or with each new batch of reagent cards 106, for example. In an exemplary embodiment, the calibration may be performed by locating the edge 136 of the reagent card 106 as described above, and then advancing the reagent card 106 a given distance through the optical signal path 158 so as to position the reagent card 106 such that the optical signal path 158 is positioned substantially between a first test strip 142 and a second test strip 142 (e.g., between a first reagent pad 140 and a second reagent pad 140). The current provided to the optical signal source 150 by the optical source interface 180 on the control line 186 may then be varied, or adjusted, so that the electrical signal indicative of the optical signal detected by the optical signal detector 154 does not saturate the output of the amplifier 200, but has sufficient energy to detect the leading end 144 and the trailing end 146 of the reagent pad 140. The strength or magnitude of the optical signal emitted by the optical signal source 150 may be controlled by varying the amount of current supplied on the control line 186, for example, for the lot of card substrate 135. Thus, the calibration results in a desired level of optical signal to enable accurate detection thresholds.

Referring now to FIGS. 7-10, in operation, an analyzer 100 may function as follows. A cartridge or cassette 104 including one or more reagent cards 106 may be loaded into the storage compartment 116, such as by opening the door 124, inserting the cassette 104 into the storage compartment 116. The door 124 may be closed to secure the storage compartment 116, for example.

The optical signal source 150 may be activated, such that the optical signal source 150 emits an optical signal, which optical signal may be detected by the optical signal detector 154 as a first optical signal. As will be appreciated by a person of ordinary skill in the art, no reagent card 106 is positioned between the optical signal source 150 and the optical signal detector 154 (e.g., in the optical signal path 158) at this stage. The optical signal detector 154 may detect the optical signal emitted by the optical signal source 150 and may generate a first electrical signal indicative of the detected first optical signal. The first electrical signal may be transmitted to the optical detector interface 182 and may be processed by the controller 162 as described above with reference to FIGS. 6-7, for example.

The analyzer 100 may operate the card stripping assembly 120 to advance a reagent card 106 at least partially out of the cassette 104 and advance the reagent card 106 towards the gate 128 (e.g., via the movable plate 132). As the leading edge 136 of the reagent card 106 is advanced and at least partially positioned between the optical signal source 150 and the optical signal detector 154 (e.g., the leading edge 136 is at least partially advanced in the optical signal path 158), the reagent card 106 interferes with the optical signal detected by the optical signal detector 154, and as a result, the optical signal detector 154 detects a second optical signal which is relatively weaker than the first optical signal, and generates a second electrical signal indicative of the second optical signal, for example. The second electrical signal may be transmitted to the optical detector interface 182 and may be processed by the controller 162, for example As the reagent card is further advanced towards the gate 128, the reagent card 106 may be advanced such that the leading end 144 of a reagent pad 140 is positioned between the optical signal source 150 and the optical signal detector 154 (e.g., the leading end 144 is at least partially positioned in the optical signal path 158) so that the pad 140 interferes with the optical signal detected by the optical signal detector 154, for example. The optical signal detector 154 may detect a third optical signal which is relatively weaker than the second optical signal described above, and may generate a third electrical signal indicative of the third optical signal, and transmit the third electrical signal to the optical detector interface 182 or to the controller 162 as described above with reference to FIGS. 6-7, for example.

The reagent card 106 may be advanced further by the card stripping assembly 120. If the reagent card 106 is the first reagent card 106 from a new lot and/or from a new cassette 104, the alignment system 122 may be calibrated by calibrating the optical signal source 150 as described above, for example. The gate raising mechanism 130 may be activated or operated by the analyzer 100 to at least partially raise the gate 128, so that the reagent card 106 may be advanced at least partially past the gate 128 and onto the travel surface 110, for example. For example, one or more reagent pads 140, or test strips 142 may be advanced past the gate 128. The gate 128 may be lowered onto the reagent card 106, for example, between adjacent reagent pads 140, as will be appreciated by persons of ordinary skill in the art having the benefit of the instant disclosure.

As the trailing end 146 of the reagent pad 140 is advanced through the optical signal path 158 and out of the optical signal path 158, the optical signal detected by the optical signal detector 154 may increase, and may become substantially equal to the second optical signal. Accordingly, the optical signal detector 154 may generate an electrical signal which may be substantially similar or substantially identical to the second electrical signal, and transmit such electrical signal to the optical detector interface 182 as described above. As will be appreciated by persons of ordinary skill in the art the advancement of subsequent reagent pads 140 through the optical signal path 158 may cause the optical signal detector 154 to alternatively detect the second optical signal and the third optical signal, and to generate and output corresponding second electrical signal and third electrical signal to the optical detector interface 182, for example. Further, as the trailing edge 138 of the reagent card 106 is advanced through the optical signal path 158, and before a leading edge 136 of a second reagent card 106 is at least partially positioned in the optical signal path 158, the optical signal detector 154 may detect the first optical signal, and may generate a signal substantially similar or equivalent to the first electrical signal, and output such electrical signal to the optical detector interface 182 as described above, for example.

As the reagent card 106 is at least partially advanced past the gate 128, the card gripper 170 may engage the reagent card 106, such that the reagent card 106 may be advanced over the travel surface 110 by the card traveling assembly 108 via the card gripper 170.

The controller 162 may operate the card travel assembly 108 to advance the reagent card 106 along the travel surface to a designated location spaced at a first distance from the optical signal path 158. For example, the distance the reagent card 106 is advanced along the travel surface 110 may be substantially equal to the first distance plus about half the width of a reagent pad 140, when such width is known. As another example, the distance the reagent card 106 is advanced along the travel surface 110 may be substantially equal to the first distance, plus about half the distance between the leading end 144 and the trailing end 146 of a reagent pad 140 as determined by the controller 162 as described above.

Figure 10:
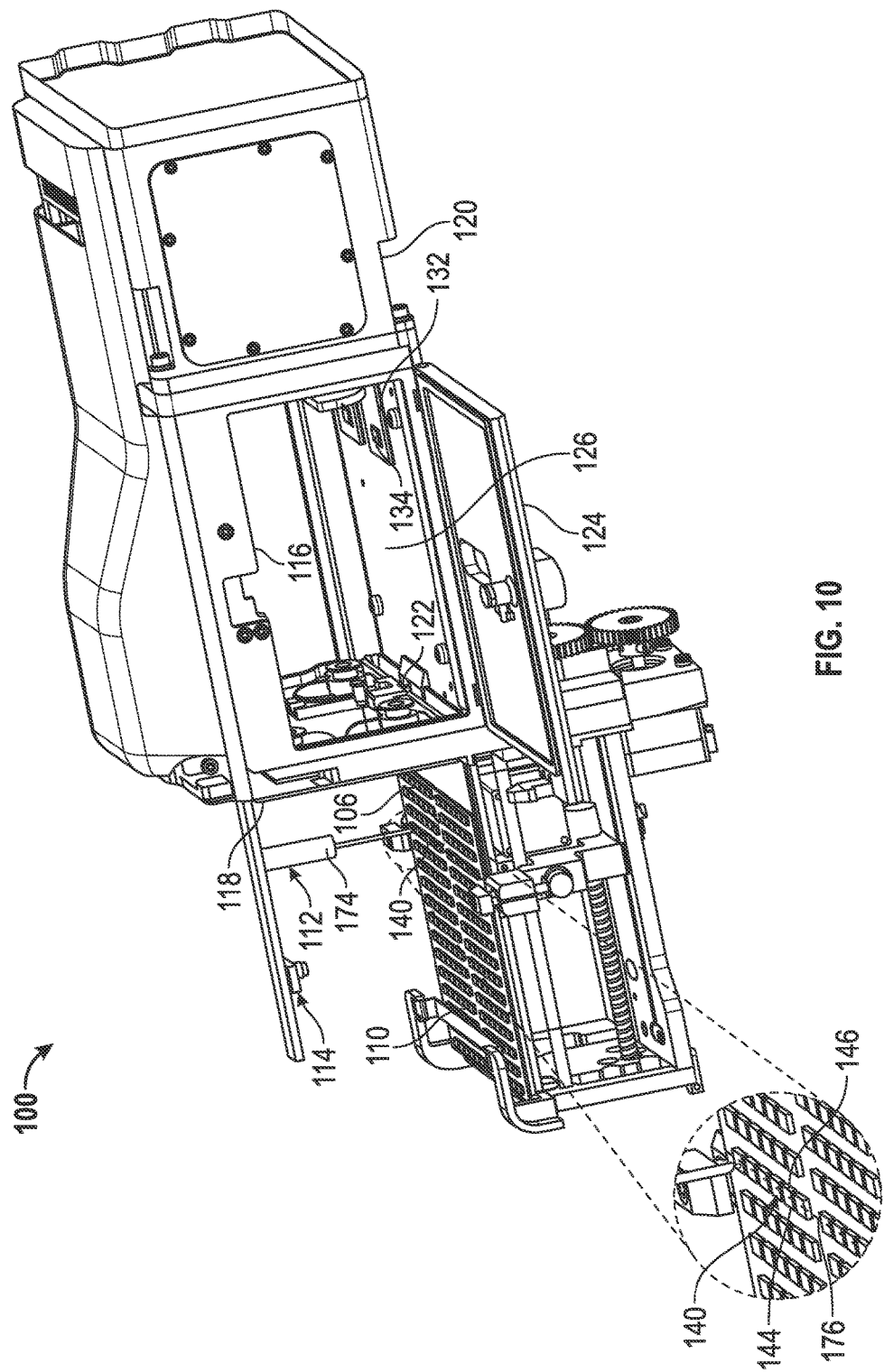
FIG. 10 is a partial perspective view of the analyzer of FIG. 8, showing the reagent card advanced along the travel surface and a sample being dispensed onto one of the reagent pads thereof.

When the reagent card 106 is advanced over the travel surface 110 so that one or more reagent pad 140 is substantially centered onto the line 176 (including a variance of between about 0 and about 50 percent of the width of the reagent pad 140, (e.g. the distance between the leading end 144 and the trailing end 146 of the reagent pad 140), a volume of sample may be dispensed onto a central region of the one or more reagent pad 140 by the sample dispenser 174 as shown in FIG. 10, for example. The substantially exact position of the one or more reagent pad 140 may be determined by the controller 162 as described above. Further, the imaging system 114 may take one or more images of the one or more reagent pad 140 at any time after the volume of sample has been dispensed on the one or more reagent pad 140, and regardless of the location of the reagent card 106 on the travel surface 110, for example. In some exemplary embodiments, an image of the one or more reagent pad 140 may be taken by the imaging system 114 concurrently with dispensing the volume of sample on the one or more reagent pad 140, before dispensing the volume of sample on the one or more reagent pad 140, immediately after dispensing the volume of sample on the one or more reagent pad 140, or at a preset time after the volume of sample is dispensed on the one or more reagent pad 140, and combinations thereof. In one exemplary embodiment, a video, or a sequence of images may be taken of the one or more reagent pad 140 as the one or more reagent pad 140 is advanced along the travel surface 110 and as a volume of sample is deposited on the one or more reagent pad 140.

In some exemplary embodiments, the imaging system 114 may take an image, a series of images, or a video, of the one or more reagent pad 140 as the one or more reagent pad 140 is positioned on the line 176, or on a designated target location or area (not shown) along the travel surface 110.

When the reagent card 106 has been advanced along the travel surface 110 by the card gripper 170 such that the trailing edge 138 of the reagent card 106 is advanced past the imaging system 114, the reagent card 106 may be removed from the travel surface 110 such as by being pushed off an edge of the travel surface 110 by the card gripper 170, and may be disposed of in any desired manner, for example. The reagent card 106 may be allowed to drop in a waste container (not shown), or may be manually removed from the analyzer 100, or combinations thereof, for example.

Two or more reagent cards 106 may be moved through the analyzer 100 in this or in similar manner. As needed or desired, a replacement cassette 104 may be inserted into the storage compartment 116 as the previous cassette 104 is emptied of the reagent cards 106 contained therein, or as different reagents cards 106 are indicated for sample analysis conducted by the analyzer 100, and combinations thereof, for example. A calibration procedure may be run with each new cassette 104 as described above.

While the inventive concepts disclosed herein have been described in connection with the exemplary embodiments of the various figures, they are not limited thereto and it is to be understood that other similar embodiments may be used or modifications and additions may be made to the described embodiments for performing the same function of the inventive concepts disclosed herein without deviating therefrom. Therefore, the inventive concepts disclosed herein should not be limited to any single embodiment, but rather should be construed in breadth and scope in accordance with the appended claims. Also, the appended claims should be construed to include other variants and embodiments of the inventive concepts disclosed herein, which may be made by those skilled in the art without departing from the true spirit and scope thereof.

From the above description, it is clear that the inventive concepts disclosed herein are well adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished within the scope of the inventive concepts disclosed and as defined in the appended claims.

The invention claimed is:

1. A reagent card analyzer, comprising:
an optical signal source configured to transmit an optical signal having a strength;
an optical signal detector at a first location, and spaced a distance from the optical signal source so that the optical signal source and the optical signal detector cooperate to define an optical signal path into which the optical signal source transmits the optical signal, the optical signal detector configured to detect the optical signal and to output an electrical signal indicative of a received strength of the optical signal;
a reader configured to read a reagent pad of a reagent card, the reagent card containing one or more reagent pads mounted onto a substrate, each reagent pad including a leading end and a trailing end;
a reagent card moving mechanism configured to move the reagent card toward the reader between the optical signal source and the optical signal detector while moving along a travel path; and
an optical detector interface electrically coupled with the optical signal detector and configured to receive a sequence of a first electrical signal, a second electrical signal and a third electrical signal from the optical signal detector with the second electrical signal being weaker than the first electrical signal, and the third electrical signal being weaker than the second electrical signal, the optical detector interface including circuitry to detect a first transition between the second electrical signal and the third electrical signal and a second transition between the first electrical signal and the second electrical signal, and to output a pad detect signal responsive to detection of the first transition, the pad detect signal indicating a substantially exact position of at least one of the leading end and the trailing end of the reagent pad as the reagent card is moved through the optical signal path; and
a controller configured to receive the pad detect signal, determine a distance to move the reagent card to position the reagent pad at a second location, and operate the reagent card moving mechanism to move the reagent pad substantially to the second location.

2. The analyzer of claim 1, wherein the optical signal path is at the first location, and further comprising a sample dispenser configured to dispense a volume of a sample at the second location separated a known distance from the first location, and wherein the card moving mechanism is configured to move the reagent card so that the reagent pad is positioned substantially at the second location based upon the pad detect signal.

3. The analyzer of claim 2, wherein the reagent pad has a central region, and wherein the sample dispenser is configured to dispense a volume of a sample on the central region of the reagent pad when the reagent pad is at the second location.

4. The analyzer of claim 2, wherein the reader comprises an imaging system configured to capture an image of the reagent pad at a third location separated at a known distance from the first location, and wherein the card moving mechanism is configured to move the reagent card so that the reagent pad is positioned substantially at the third location based upon the pad detect signal.

5. The analyzer of claim 1, wherein the optical signal has a wavelength of about 850 nanometers.

6. The analyzer of claim 1, wherein the optical signal source includes a vertical cavity surface emitting laser.

7. The analyzer of claim 6, wherein the vertical cavity surface emitting laser is configured to transmit an optical signal including a beam having an angular spread of less than about 2°.

8. The reagent card analyzer of claim 1, wherein the reagent card contains a sequence of reagent pads mounted onto the substrate in position to interfere with the optical signal as the reagent card is moved along the travel path, and wherein the circuitry of the optical detector interface detects multiple transitions between first electrical signals and second electrical signals, and outputs a sequence of pad detect signals indicative of at least one of the leading end and the trailing end of each reagent pad in the sequence of reagent pads.

9. A reagent card analyzer, comprising:
an optical signal source attached to a support and configured to transmit an optical signal having a strength;
an optical signal detector at a first location and attached to the support and spaced at a distance from the optical signal source so that the optical signal source and the optical signal detector cooperate to define an optical signal path into which the optical signal source transmits the optical signal, the optical signal detector configured to detect the optical signal and to output an electrical signal indicative of a received strength of the optical signal;
a reader configured to read one or more reagent pad of a reagent card, the reagent card containing one or more reagent pads mounted onto a substrate, each reagent pad including a leading end and a trailing end, the reader positioned at a second location a known distance from the first location;
a sample dispenser configured to dispense a volume of sample on the one or more reagent pad of the reagent card, the sample dispenser positioned at a third location;
a reagent card moving mechanism configured to move the reagent card toward the reader between the optical signal source and the optical signal detector while moving along a travel path so that the reagent card interferes with the optical signal, and to move the reagent card so as to position the one or more reagent pad substantially at the second and the third location;
an optical detector interface electrically coupled with the optical signal detector and configured to receive a sequence of first, second and third electrical signals from the optical signal detector with the second electrical signal being weaker than the first electrical signal, and the third electrical signal being weaker than the second electrical signal, the optical detector interface including circuitry to detect a first transition between the second electrical signal and the third electrical signal and a second transition between the first electrical signal and the second electrical signal, and to output a pad detect signal responsive to detection of the first transition, the pad detect signal indicating a substantially exact position of at least one of the leading end and the trailing end of the reagent pad as the reagent card is moved through the optical signal path between the optical signal source and the optical signal detector; and a controller configured to control the reader, the sample dispenser, and the card moving mechanism, the controller electrically coupled with the optical detector interface, wherein the controller is configured to receive the pad detect signal, determine a distance to move the reagent card to position the reagent pad at the second location, and operate the card moving mechanism to move the one or more reagent card so that the one or more reagent pad is positioned substantially at the second location.

10. The analyzer of claim 9, wherein the one or more reagent pad has a central region, and wherein the sample dispenser is configured to dispense a volume of a sample on the central region of the one or more reagent pad.

11. The analyzer of claim 9, wherein the reader comprises an imaging system configured to capture an image of the one or more reagent pad at the third location.

12. The analyzer of claim 9, wherein the optical signal has a wavelength of about 850 nanometers.

13. The analyzer of claim 9, wherein the optical signal source includes a vertical cavity surface emitting laser.

14. The analyzer of claim 13, wherein the vertical cavity surface emitting laser is configured to transmit an optical signal including a beam having an angular spread of less than about 2°.

* * * * *